United States Patent
Ling et al.

(10) Patent No.: US 11,376,274 B2
(45) Date of Patent: Jul. 5, 2022

(54) JOINT CAVITY INJECTION PREPARATION AND USE THEREOF

(71) Applicants: SHANDONG ACADEMY OF PHARMACEUTICAL SCIENCES, Jinan (CN); SHANDONG FREDA PHARMACEUTICAL GROUP CO., LTD., Jinan (CN)

(72) Inventors: Peixue Ling, Jinan (CN); Fei Liu, Jinan (CN); Huarong Shao, Jinan (CN); Lei Chen, Jinan (CN); Zhiyun Zhang, Jinan (CN); Xiaoyuan Zhang, Jinan (CN); Qixin Chen, Jinan (CN); Guanying Han, Jinan (CN); Yanling Cheng, Jinan (CN); Jianqiang Zhang, Jinan (CN); Daizhou Zhang, Jinan (CN)

(73) Assignees: SHANDONG ACADEMY OF PHARMACEUTICAL SCIENCES, Jinan (CN); SHANDONG FREDA PHARMACEUTICAL GROUP CO., LTD., Jinan (CN)

( * ) Notice: Subject to any disclaimer, the term of this patent is extended or adjusted under 35 U.S.C. 154(b) by 0 days.

(21) Appl. No.: 17/297,467

(22) PCT Filed: May 21, 2019

(86) PCT No.: PCT/CN2019/087849
§ 371 (c)(1),
(2) Date: May 27, 2021

(87) PCT Pub. No.: WO2020/107820
PCT Pub. Date: Jun. 4, 2020

(65) Prior Publication Data
US 2021/0353662 A1 Nov. 18, 2021

(30) Foreign Application Priority Data
Nov. 30, 2018 (CN) .......................... 201811455378.5

(51) Int. Cl.
A61K 31/723 (2006.01)
A61P 19/02 (2006.01)
A61K 31/722 (2006.01)
A61K 31/728 (2006.01)
A61K 31/737 (2006.01)
A61K 9/00 (2006.01)
A61K 31/7016 (2006.01)

(52) U.S. Cl.
CPC .......... *A61K 31/723* (2013.01); *A61K 9/0019* (2013.01); *A61K 31/7016* (2013.01); *A61K 31/722* (2013.01); *A61K 31/728* (2013.01); *A61K 31/737* (2013.01); *A61P 19/02* (2018.01)

(58) Field of Classification Search
CPC .......................... A61K 31/723; C08B 37/0033
See application file for complete search history.

(56) References Cited

U.S. PATENT DOCUMENTS 8,623,839 B2 * 1/2014 Su .......................... A61P 19/04
514/54

FOREIGN PATENT DOCUMENTS

| CN | 101940587 A | 1/2011 |
|---|---|---|
| CN | 102946855 A | 2/2013 |
| CN | 105251048 A | 1/2016 |
| CN | 106692179 A | 5/2017 |
| CN | 109260219 A | 1/2019 |

OTHER PUBLICATIONS

Machine translation of CN 10669217A. (Year: 2017).*
Wang, F. et al "Conformation role of xanthan gum . . . " Food Chem. Toxicol., vol. 67, No. 9, pp. 3289-3294. (Year: 2002).*
Rivera, F. et al "Effectiveness of intra-articular injections . . . " J. Orthopaed. Traumatol., vol. 17, pp. 27-33. (Year: 2016).*
Tako, M. et al "Rheological properties of deacetylated xanthan . . . " Agric. Biol. Chem., vol. 48, No. 12, pp. 2987-2993. (Year: 1984).*
Chen, Q. et al "Recent advances in polysaccharides for osteoarthritis therapy" Eur. J. Med. Chem., vol. 139, pp. 926-935. (Year: 2017).*

* cited by examiner

*Primary Examiner* — Leigh C Maier
(74) *Attorney, Agent, or Firm* — Bayramoglu Law Offices LLC

(57) ABSTRACT

A joint cavity injection preparation is provided. The active ingredient of the joint cavity injection preparation is deacetylated xanthan gum (XG). The deacetylated XG has a molecular weight of 500,000 to 20,000,000. The joint cavity injection preparation is prepared from deacetylated xanthan gum (XG), which has higher biocompatibility and safe wide-dosage range than existing joint cavity injection preparations prepared from XG.

12 Claims, No Drawings

JOINT CAVITY INJECTION PREPARATION AND USE THEREOF

CROSS REFERENCE TO THE RELATED APPLICATIONS

This application is the national phase entry of International Application No. PCT/CN2019/087849, filed on May 21, 2019, which is based upon and claims priority to Chinese Patent Application No. 201811455378.5, filed on Nov. 30, 2018, the entire contents of which are incorporated herein by reference.

TECHNICAL FIELD

The present disclosure relates to the technical field of orthopedic medicine, and in particular to a joint cavity injection preparation and use thereof.

BACKGROUND

Osteoarthritis (OA) is a common degenerative joint disease (DJD) characterized by articular cartilage destruction and hyperosteogeny, with a relatively-high incidence among elderly people. With the population aging and the obese population increasing in China, the incidence of OA continues to rise. In OA pathology, the viscoelasticity of synovial fluid is significantly reduced, and cartilage is degraded and destroyed, resulting in joint dysfunction.

Viscosupplementation is one of the main clinical treatment methods for OA, where exogenous hyaluronic acid (HA) is injected into a joint cavity to restore the lubricating and buffering function of synovial fluid, promote cartilage tissue repair, relieve OA symptoms, and improve the physiological functions of a joint. Since HA is easily degraded by hyaluronidase and free radicals in the body, it stays in the joint cavity for a short time. Therefore, developing new viscosupplementation agents with similar viscoelasticity and high stability for OA treatment is of great significance to reducing administration frequency, avoiding infection caused by repeated injections, and improving patient compliance.

Xanthan gum (XG) is a biopolymer polysaccharide, which is similar to HA, and has prominent viscoelasticity and higher stability than HA. XG is a water-soluble extracellular polysaccharide (EPS) produced by the fermentation of *Xanthomonas campestris* with sugars as a main raw material. XG has a relative molecular mass (Mr) of $2 \times 10^6$ to $2 \times 10^7$. An XG molecule has a basic structure composed of pentose repeating units. In an XG molecule, the main chain is formed by D-glucose residues linked via β-1,4 bonds, and the side chain is a trisaccharide formed by D-mannose and D-glucuronic acid alternately linked, where the mannose attached to the main chain is partially acetylated at the position of C-6, and the mannose at the terminals of some side chains is connected with a pyruvate group at the positions of C-4 and C-6; a secondary structure is a double-helix or multi-helix structure maintained via hydrogen bonds where the trisaccharide side chains are reversely wound around the main chain; and a tertiary structure is a network structure formed by secondary helix structures linked via non-covalent bonds. The structure and conformation of XG determine the functional properties of a solution of XG: the complex aggregation structure and intermolecular forces of XG make an XG solution have high viscosity under low shearing force and low concentration, show higher modulus than other polysaccharide solutions, and have pseudoplastic behaviors; and the hard linear molecular chain, hydrogen bonds and anions on the molecular chain, and the protection of entangled side chains on the main chain in XG make an XG solution have prominent heat resistance and salt resistance and exhibit high stability under acid, alkali, and enzymolysis conditions. Generally, in XG, the pyruvate substituent has a content of 30% to 40%, and the acetylated group has a content of 60% to 70%; and the two are irregularly distributed on the chain, which have a great influence on the conformation and physicochemical properties of XG. The removal of either the acetyl group or the pyruvate group from XG will significantly change the properties of XG. According to rheological studies, XG molecules where pyruvate groups are removed have significantly-reduced intermolecular forces. The pyruvate groups in XG molecules may form hydrogen bonds with each other and may also form hydrogen bonds with acetyl groups on adjacent side chains to stabilize the molecular structure of XG. The acetyl group is generally considered to provide intramolecular interaction, so XG molecules where acetyl groups are removed become more flexible.

Preliminary research in the laboratory shows that XG injection into a joint cavity shows a long-term therapeutic effect on experimental OA, which can reduce the number of administrations; and XG has the potential to be developed into a new drug for OA treatment. An XG solution has specific rheological properties, especially the properties and viscoelasticity of non-Newtonian fluids: when a joint is at a low impact frequency, the XG solution is a viscous solution that exhibits a lubricating function on the synovial tissue, various tissue planes, ligaments, and collagen structures in the joint, thus reducing the friction among tissues; and when a joint is at a high impact frequency, the viscous characteristic is converted into an elastic characteristic to buffer the impact of a stress on the joint. XG can form a macromolecular network structure in the synovial fluid, which can regulate the diffusion of water and macromolecular substances, act as a diffusion barrier in a joint, play a role of barrier for bacteria, toxins, immune complexes, etc., protect cartilage and synovium from being damaged by enzymes, chemicals, toxins, etc., and stabilize cell membranes and deactivate the sensitivity of cell membrane receptors. There have been reports in the prior art that XG preparations can provide long-term treatment for OA. The patent 2017100752628 discloses a pharmaceutical preparation with low-molecular-weight XG for joint cavity injection and a preparation method thereof. The pharmaceutical preparation that includes low-molecular-weight XG with a relative molecular weight of 100,000 to 1,990,000 can be used to prevent rheumatism, rheumatoid arthritis (RA), and OA, which can protect articular cartilage in OA joint and repair damaged articular cartilage. The patent mainly solves the problem that XG with a conventional molecular weight (relative molecular weight of 2,000,000 to 20,000,000) is not easily degraded by enzymes and free radicals in the body due to high stability and thus can hardly be excreted by the body's metabolism. However, when a low-molecular-weight XG pharmaceutical preparation is used in the treatment of OA, the preparation enters visceral tissues through the blood circulation after being injected into a joint cavity and stays in the tissues for a relatively-long time due to a stable structure, and it takes a relatively long time to clear the preparation. Moreover, the long-term repeated injection of the low-molecular-weight XG pharmaceutical preparation at a high dosage tends to cause increased spleen weight and increased number of monocytes, and the pharmaceutical preparation has poor biocompatibility, which seriously affects the use effect and hinders the further use. However, using deacetylated XG with an equivalent molecular weight, even deacetylated XG with higher molecular weight and concentration can solve the above problems while ensuring excellent therapeutic effects.

SUMMARY

The present disclosure provides a joint cavity injection preparation and use thereof. The joint cavity injection preparation includes deacetylated XG as an active ingredient for treating OA, which exhibits excellent treatment effect and avoids adverse reactions caused by the existing long-term repeated injection of high-dosage XG. The joint cavity injection preparation has excellent biocompatibility, safe wide-dosage range, and high safety use, and solves the problems existing in the prior art.

In one aspect, the present disclosure provides a joint cavity injection preparation, and an active ingredient of the preparation is deacetylated XG.

A percentage of a mass of the deacetylated XG in a volume of the joint cavity injection preparation may be 0.01% to 10% (w/v), preferably 0.5% to 8% (w/v), and more preferably 1% to 5% (w/v).

The deacetylated XG may have a molecular weight of 100,000 to 20,000,000, preferably of 500,000 to 1,0000,000, and more preferably of 800,000 to 3,000,000.

The preparation may further include one or more from the group consisting of sodium hyaluronate (SH), chondroitin sulfate (CS), chitosan, and trehalose.

The preparation may further include disodium phosphate (DSP), monosodium phosphate (MSP), sodium chloride, and water for injection (WFI).

The preparation may include the following components, in mass-volume percentage: deacetylated XG: 1% to 5%, DSP: 0.4% to 0.7%, MSP: 0.1% to 0.16%, sodium chloride; 0.25% to 0.41%, and WFI: the balance.

The preparation may have a pH of 5.5 to 9 and an osmotic pressure of 200 mOsmol/L to 400 mOsmol/L.

In another aspect, the present disclosure also provides use of deacetylated XG in the preparation of a drug for treating OA.

A drug for treating OA prepared from deacetylated XG has higher biosafety than a drug for treating OA prepared from XG. In general, regardless of the molecular weights and dosages of deacetylated XG and ordinary XG, a drug prepared from deacetylated XG has higher biosafety than a drug prepared from XG. In particular, when deacetylated XG and ordinary XG with comparable molecular weights are used to prepare drugs for treating OA at comparable dosages, the former shows biosafety significantly better than that of the latter. For example, when deacetylated XG and XG with an average molecular weight of 1,000,000 are used at the same dosage (5%), the deacetylated XG shows biosafety significantly higher than that of XG.

The deacetylated XG may be used at an amount of 0.01% to 10% (w/v), preferably of 0.5% to 8% (w/v), and more preferably of 1% to 5% (w/v) in the drug; and the deacetylated XG may have a molecular weight of 100,000 to 20,000,000, preferably of 500,000 to 10,000,000, and more preferably of 800,000 to 3,000,000.

The drug may have a dosage form selected from the group consisting of injection, gel, ointment, aerosol, and spray.

The present disclosure also provides a method for preparing a joint cavity injection preparation, including using deacetylated XG as an active ingredient to prepare the injection preparation. The deacetylated XG in the present disclosure can be commercially-available deacetylated XG, or can be prepared by the following preparation method:

(1) adjusting a pH of an XG aqueous solution with a mass fraction of 1% to 10% and a relative molecular weight of 1,000,000 to 20,000,000 to 10 to 13, and stirring for 0.2 h to 2 h at 50° C. to 100° C.;

(2) adjusting a pH of a resulting solution to 1.5 to 7, and reacting at 0.05 MPa to 0.15 MPa for 10 min to 30 min; and (3) cooling, adjusting a pH to 7.0, and precipitating with ethanol to obtain a precipitate.

The above-mentioned preparation of deacetylated XG may further include drying the precipitate obtained in step (3).

The joint cavity injection preparation prepared by the above method may have a pH of 5.5 to 9 and an osmotic pressure of 200 mOsmol/L to 400 mOsmol/L.

BENEFICIAL EFFECTS OF THE PRESENT DISCLOSURE

In the present disclosure, deacetylated XG with different conformation and physicochemical properties from XG is used instead of XG to produce drugs and preparations for OA; and obtained drugs and joint cavity injection preparations for treating OA have superior biocompatibility and safety. Compared with XG, deacetylated XG, when used in the production of drugs and preparations for OA at an equivalent molecular weight and concentration or a higher molecular weight and concentration, can well solve the problem that poor biocompatibility is caused by slow clearance of XG in the body due to a stable structure, which provides a new way for the development of new drugs such as OA drugs and joint cavity injection preparations.

DETAILED DESCRIPTION OF THE EMBODIMENTS

In order to clearly explain the technical features of the solution, the present disclosure will be described in detail below through specific examples.

Example 1

A preparation method of deacetylated XG was provided:
10 g of XG with a molecular weight of 3,000,000 was taken and fully dissolved in 1,000 mL of water, a pH was adjusted to 11, and a resulting solution was stirred at 50° C. for 0.5 h; a pH was adjusted to 2.0, and a resulting mixture reacted at 0.1 MPa for 20 min and then cooled; a pH was adjusted to 7.0, and precipitation was conducted with ethanol; and a precipitate product was dried at 40° C. under reduced pressure for 24 h to obtain the deacetylated XG.

According to multi-angle laser test, the deacetylated XG had Mw of 1,000,000, and according to hydroxylamine hydrochloride colorimetry, there were no acetyl groups in a structure of the deacetylated XG.

Example 2

A preparation method of deacetylated XG was provided:
20 g of XG with a molecular weight of 3,000,000 was taken and fully dissolved in 1,000 mL of water, a pH was adjusted to 11, and a resulting solution was stirred at 60° C. for 2 h; a pH was adjusted to 3.0, and a resulting mixture reacted at 0.1 MPa for 30 min and then cooled; a pH was adjusted to 7.0, and precipitation was conducted with ethanol; and a precipitate product was dried at 40° C. under reduced pressure for 24 h to obtain the deacetylated XG.

According to multi-angle laser test, the deacetylated XG had Mw of 2,000,000, and according to hydroxylamine hydrochloride colorimetry, there were no acetyl groups in a structure of the deacetylated XG.

Example 3

A preparation method of deacetylated XG was provided:
30 g of XG with a molecular weight of 5,000,000 was taken and fully dissolved in 1,000 mL of water, a pH was adjusted to 12, and a resulting solution was stirred at 50° C. for 1 h; a pH was adjusted to 5.0, and a resulting mixture reacted at 0.1 MPa for 20 min and then cooled; a pH was adjusted to 7.0, and precipitation was conducted with ethanol; and a precipitate product was dried at 40° C. under reduced pressure for 24 h to obtain the deacetylated XG.

According to multi-angle laser test, the deacetylated XG had Mw of 4,000,000, and according to hydroxylamine hydrochloride colorimetry, there were no acetyl groups in a structure of the deacetylated XG.

Example 4

A preparation method of deacetylated XG was provided:
50 g of XG with a molecular weight of 5,000,000 was taken and fully dissolved in 1,000 mL of water, a pH was adjusted to 11, and a resulting solution was stirred at 55° C. for 0.5 h; a pH was adjusted to 7.0, and a resulting mixture reacted at 0.1 MPa for 20 min and then cooled; a pH was adjusted to 7.0, and precipitation was conducted with ethanol; and a precipitate product was dried at 40° C. under reduced pressure for 24 h to obtain the deacetylated XG.

According to multi-angle laser test, the deacetylated XG had Mw of 5,000,000, and according to hydroxylamine hydrochloride colorimetry, there were no acetyl groups in a structure of the deacetylated XG.

Example 5

A preparation method of deacetylated XG was provided:
50 g of XG with a molecular weight of 8,000,000 was taken and fully dissolved in 1,000 mL of water, a pH was adjusted to 11, and a resulting solution was stirred at 55° C. for 0.5 h; a pH was adjusted to 2.0, and a resulting mixture reacted at 0.1 MPa for 30 min and then cooled; a pH was adjusted to 7.0, and precipitation was conducted with ethanol; and a precipitate product was dried at 40° C. under reduced pressure for 24 h to obtain the deacetylated XG.

According to multi-angle laser test, the deacetylated XG had Mw of 2,600,000, and according to hydroxylamine hydrochloride colorimetry, there were no acetyl groups in a structure of the deacetylated XG.

The deacetylated XG products prepared by the above methods were used to prepare joint cavity injection preparations:

Example 6

Joint Cavity Injection Preparation with 1% Deacetylated XG

| | |
|---|---|
| Deacetylated XG (with an average molecular weight of 1,000,000) | 5 g |
| DSP | 3.78 g |
| MSP | 0.8 g |
| Sodium chloride | 2.055 g |
| WFI | add to 500 mL |
| pH | 7.4 |
| Osmotic pressure | 300 mOsmol/L |

Example 7

Joint Cavity Injection Preparation with 3% Deacetylated XG

| | |
|---|---|
| Deacetylated XG (with an average molecular weight of 1,000,000) | 15 g |
| DSP | 3.00 g |
| MSP | 0.6 g |
| Sodium chloride | 1.65 g |
| WFI | add to 500 mL |
| pH | 7.4 |
| Osmotic pressure | 300 mOsmol/L |

Example 8

Joint Cavity Injection Preparation with 5% Deacetylated XG

| | |
|---|---|
| Deacetylated XG (with an average molecular weight of 1,000,000) | 25 g |
| DSP | 2.5 g |
| MSP | 0.5 g |
| Sodium chloride | 1.36 g |
| WFI | add to 500 mL |
| pH | 7.4 |
| Osmotic pressure | 300 mOsmol/L |

Example 9

Joint Cavity Injection Preparation with 1% Deacetylated XG

| | |
|---|---|
| Deacetylated XG (with an average molecular weight of 1,000,000) | 5 g |
| DSP | 3.0 g |
| MSP | 0.7 g |
| Sodium chloride | 1.60 g |
| WFI | add to 500 mL |
| pH | 7.4 |
| Osmotic pressure | 300 mOsmol/L |

Example 10

Joint Cavity Injection Preparation with 5% Deacetylated XG

| | |
|---|---|
| Deacetylated XG (with an average molecular weight of 1,000,000) | 25 g |
| DSP | 2.4 g |
| MSP | 0.6 g |
| Sodium chloride | 1.20 g |
| WFI | add to 500 mL |
| pH | 7.4 |
| Osmotic pressure | 300 mOsmol/L |

Experimental Study:

1. Animal Experiments to Study the Treatment Effects of the Above Deacetylated XG Joint Cavity Injection Preparations on OA:

64 New Zealand big-eared white rabbits were randomly divided into 8 groups, each with 8 rabbits (half male and half female): normal control group, negative control group (normal saline (NS)), deacetylated XG group 1 (Example 6, 1%, 1,000,000), deacetylated XG group 2 (Example 7, 3%, 1,000,000), deacetylated XG group 3 (Example 8, 5%, 1,000,000), deacetylated XG group 4 (Example 9, 1%, 5,000,000), ordinary XG group (1%, 1,000,000), and SH control group.

The left knee ligament was cut by anterior cruciate ligament transection (ACLT) to establish knee OA models, and after the models were successfully established, the joint cavities were injected with the corresponding drugs or NS at a dosage of 0.3 mL/joint. The SH control group was administered once a week, with a total of 5 administrations; and the deacetylated XG groups and the ordinary XG group were administered once every 5 weeks, with a total of 2 administrations. Animals in each group were sacrificed 10 weeks after the first administration, the articular cartilage was subjected to pathological observation and scored, and scoring results were shown in Table 1. The results showed that, when administered once every 5 weeks, both deacetylated XG and ordinary XG exhibited significant therapeutic effects on OA, which had no significant difference from the SH group administered once a week. The pathological scores of articular cartilage were shown in Table 1.

TABLE 1

Pathological scores of articular cartilage

| Group | Pathological score |
|---|---|
| Normal group | 0.82 ± 0.05 |
| Negative control group | 10.26 ± 0.64 |
| SH group | 4.89 ± 0.32 |
| Ordinary XG group (1%, 1,000,000) | 4.91 ± 0.18 |
| Deacetviated XG group 1 (1%, 1,000,000) | 4.87 ± 0.42 |
| Deacetyiated XG group 2 (3%, 1,000,000) | 4.36 ± 0.51 |
| Deacetylated XG group 3 (5%, 1,000,000) | 4.01 ± 0.36 |
| Deacetylated XG group 4 (1%, 5,000,000) | 4.22 ± 0.41 |

2. Research on the Influence of the Above Deacetylated XG Joint Cavity Injection Preparations on the Lubricating Effect of Bovine Articular Cartilage:

Bovine articular cartilage was peeled off by a special bovine bone steel knife and prepared into cartilage masses with uniform thickness (1.89 mm). The tribological indexes under lubrication of different injection preparations were tested on a reciprocating friction testing machine, including the following: dry friction group, NS group, SH group, deacetylated XG group 1 (Example 6, 1%, 1,000,000), deacetylated XG group 2 (Example 7,3%, 1,000,000), deacetylated XG group 3 (Example 8, 5%, 1,000,000), deacetylated XG group 4 (Example 9, 1%, 5,000,000), ordinary XG group (1%, 1,000,000), and SH control group. Parameters of the testing machine were set as follows: test force: 3 N, and reciprocating frequency: 1 Hz. Test results were shown in Table 2 below.

TABLE 2

Influence on the lubricating effect of bovine articular cartilage

| Group | Pathological score |
|---|---|
| Dry friction group | 0.342 ± 0.09 |
| NS group | 0.151 ± 0.08 |
| SH group | 0.113 ± 0.06 |
| Ordinary XG group (1%, 1,000,000) | 0.081 ± 0.05 |
| Deacetylated XG group 1 (1%, 1,000,000) | 0.083 ± 0.07 |
| Deacetylated XG group 2 (3%, 1,000,000) | 0.073 ± 0.06 |
| Deacetylated XG group 3 (5%, 1,000,000) | 0.064 ± 0.08 |
| Deacetylated XG group 4 (1%, 5,000,000) | 0.071 ± 0.10 |

It can be seen from the results that, on the reciprocating friction testing machine, the bovine knee articular cartilage showed lubricating effects under the lubrication of deacetylated XG and ordinary XG better than that under the lubrication of SH.

3. Research on the Biocompatibility of the Above Deacetylated XG Joint Cavity Injection Preparations:

80 SD rats were randomly divided into 8 groups, each with 10 rats (half male and half female): negative control group (NS), deacetylated XG group 1 (Example 6, 1%, 1,000,000), deacetylated XG group 2 (Example 7, 3%, 1,000,000), deacetylated XG group 3 (Example 8, 5%, 1,000,000), deacetylated XG group 4 (Example 9, 1%, 5,000,000), deacetylated XG group 5 (Example 10, 5%, 5,000,000), ordinary XG group 1 (5%, 1,000,000), and ordinary XG group 2 (5%, 5,000,000). The joint cavities were injected with the corresponding drugs or NS once every 2 weeks at a dosage of 0.06 mL/joint, and the administration lasted for 6 months. Two weeks after the last administration, animals were anesthetized and blood was collected for blood routine examination; and animals were sacrificed, spleens were collected and weighed to calculate an organ coefficient (%).

Results showed that the injection of ordinary XG caused a significant increase in spleen weight and monocyte proportion, but the repeated injection of high-dosage deacetylated XG did not cause adverse reactions of organs and tissues and abnormal results of blood routine examination.

The above experiments show that the long-term repeated injection of high-dosage XG caused adverse reactions such as increase in spleen weight and monocyte proportion, but the long-term repeated injection of high-dosage deacetylated XG caused no adverse reactions, which indicates that the deacetylated XG has a safe dosage range for OA treatment that is significantly wider than that of ordinary XG, and also has a significant advantage in biocompatibility.

TABLE 3

Influence of deacetylated XG on monocytes

| Group | Monocyte number | Monocyte proportion |
|---|---|---|
| NS group | 0.30 ± 0.04 | 3.20 ± 0.73 |
| Ordinary XG group (5%, 1,000,000) | 0.38 ± 0.11 | 3.85 ± 0.88 |
| Ordinary XG group (5%, 5,000,000) | 0.67 ± 0.15 | 5.25 ± 1.24 |
| Deacetylated XG group 1 (1%, 1,000,000) | 0.31 ± 0.03 | 3.18 ± 0.69 |

TABLE 3-continued

Influence of deacetylated XG on monocytes

| Group | Monocyte number | Monocyte proportion |
|---|---|---|
| Deacetylated XG group 2 (3%, 1,000,000) | 0.29 ± 0.05 | 3.17 ± 0.78 |
| Deacetylated XG group 3 (5%, 1,000,000) | 0.32 ± 0.03 | 3.31 ± 0.65 |
| Deacetylated XG group 4 (1%, 5,000,000) | 0.34 ± 0.05 | 3.51 ± 0.77 |
| Deacetylated XG group 5 (5%, 5,000,000) | 0.35 ± 0.09 | 3.69 ± 0.87 |

TABLE 4

Influence of deacetylated XG on spleen weight

| Group | Spleen weight (g) | Organ coefficient (%) |
|---|---|---|
| NS group | 1.301 ± 0.12 | 0.26 ± 0.05 |
| Ordinary XG group (5%, 1,000,000) | 1.339 ± 0.11 | 0.28 ± 0.04 |
| Ordinary XG group (5%, 5,000,000) | 1.591 ± 0.15 | 0.35 ± 0.04 |
| Deacetylated XG group 1 (1%, 1,000,000) | 1.283 ± 0.17 | 0.25 ± 0.05 |
| Deacetylated XG group 2 (3%, 1,000,000) | 1.302 ± 0.23 | 0.26 ± 0.06 |
| Deacetylated XG group 3 (5%, 1,000,000) | 1.300 ± 0.09 | 0.25 ± 0.03 |
| Deacetylated XG group 4 (1%, 5,000,000) | 1.298 ± 0.08 | 0.26 ± 0.04 |
| Deacetylated XG group 5 (5%, 5,000,000) | 1.314 ± 0.13 | 0.27 ± 0.04 |

The above implementations should not be considered as a limitation on the protection scope of the present disclosure. It should be appreciated by those skilled in the art that any alternative improvement or change made to the implementations of the present disclosure falls within the protection scope of the present disclosure.

Anything not described in detail in the present disclosure may be a widely-known technology for those skilled in the art.

What is claimed is:

1. A joint cavity injection preparation, wherein
   an active ingredient of the joint cavity injection preparation is deacetylated xanthan gum (XG);
   the deacetylated XG has a molecular weight of 5,000,000 to 10,000,000; and
   a percentage of a mass of the deacetylated XG in a volume of the joint cavity injection preparation is 3% to 5% (w/v);
   wherein the joint cavity injection preparation further comprises disodium phosphate (DSP) and monosodium phosphate (MSP).

2. The joint cavity injection preparation according to claim 1, further comprising
   one or more selected from the group consisting of sodium hyaluronate (SH), chondroitin sulfate (CS), chitosan, and trehalose.

3. The joint cavity injection preparation according to claim 1, wherein
   the joint cavity injection preparation has a pH of 5.5 to 9 and an osmotic pressure of 200 mOsmol/L to 400 mOsmol/L.

4. A method of treating osteoarthritis (OA), comprising the step of treating the OA with deacetylated xanthan gum (XG) in a preparation of a drug, wherein
   the deacetylated XG has a molecular weight of 5,000,000 to 10,000,000;
   the deacetylated XG is used at an amount of 3% to 5% (w/v); and
   the drug has a dosage form of a joint cavity injection preparation.

5. The method of treating the OA according to claim 4, wherein the drug has higher biosafety than a drug for treating the OA prepared from XG.

6. The joint cavity injection preparation according to claim 1, further comprising sodium hyaluronate (SH), chondroitin sulfate (CS), and chitosan.

7. The joint cavity injection preparation according to claim 1, further comprising sodium hyaluronate (SH), chondroitin sulfate (CS), and trehalose.

8. The Joint cavity injection preparation according to claim 1, further comprising sodium hyaluronate (SH), chondroitin sulfate (CS), chitosan, and trehalose.

9. The joint cavity injection preparation according to claim 2, comprising chitosan.

10. The joint cavity injection preparation according to claim 2, comprising trehalose.

11. The joint cavity injection preparation according to claim 2, comprising chitosan and trehalose.

12. The method of claim 4, wherein the joint cavity injection preparation further comprises disodium phosphate (DSP) and monosodium phosphate (MSP).

* * * * *